United States Patent [19]
Levy et al.

[11] Patent Number: 5,318,562
[45] Date of Patent: Jun. 7, 1994

[54] HANDPIECE FOR DELIVERING LASER RADIATION

[75] Inventors: Guy Levy, Tustin; James H. Tillotson, Rancho Mirage; William A. Gollihar, Moreno Valley, all of Calif.

[73] Assignee: Laser Endo Technic Corporation, San Clemente, Calif.

[21] Appl. No.: 848,179

[22] Filed: Mar. 10, 1992

[51] Int. Cl.$^5$ .................................................. A61B 17/36
[52] U.S. Cl. ......................................... 606/16; 606/13; 606/17; 607/89
[58] Field of Search ............... 128/395, 396, 397, 398; 606/2, 3, 6, 7, 10, 11, 12, 13, 14, 15, 16, 17; 607/88, 89

[56] References Cited

U.S. PATENT DOCUMENTS

| | | | |
|---|---|---|---|
| 3,821,510 | 6/1974 | Muncheryan | 128/395 |
| 4,273,535 | 6/1981 | Yamamoto et al. | 128/395 |
| 4,503,853 | 3/1985 | Ota et al. | 128/395 |
| 4,538,609 | 9/1985 | Takenaka et al. | 128/395 |
| 4,608,980 | 9/1986 | Aihara | 606/16 |
| 4,671,273 | 6/1987 | Lindsey | 606/16 |
| 4,676,242 | 6/1987 | Doi | 128/398 |
| 4,694,828 | 9/1987 | Eichenbaum | 606/6 |
| 4,826,431 | 5/1989 | Fujimura et al. | 128/395 |
| 4,832,024 | 5/1989 | Boussignac et al. | 606/7 |
| 4,849,859 | 7/1989 | Nagasawa | 128/395 |
| 4,895,145 | 1/1990 | Joffe et al. | 606/11 |
| 5,074,861 | 12/1991 | Schneider et al. | 606/17 |

OTHER PUBLICATIONS

"Introduction of New Dental Oral Yag Laser Handpiece and its Clinical Application" by Yoshida et al., Lasers in Dentistry, Elsevier Science Publishers B.V.; May, 1989.

*Primary Examiner*—Stephen C. Pellegrino
*Assistant Examiner*—M. Peffley
*Attorney, Agent, or Firm*—Spensley Horn Jubas & Lubitz

[57] ABSTRACT

A medical or dental handpiece for the performance of laser radiation treatments, composed of: an elongate housing constructed to be held in the hand, the housing having a radiation delivery end and enclosing a chamber which is adjacent the radiation delivery end; a radiation conducting element disposed in the housing for conducting laser radiation from a laser source into the chamber and toward the radiation delivery end; and a gas flow path in the chamber for guiding a flow of cooling gas through the chamber in a direction from the radiation conducting element toward the radiation delivery end.

7 Claims, 3 Drawing Sheets

HANDPIECE FOR DELIVERING LASER RADIATION

BACKGROUND OF THE INVENTION

The present invention is directed to medical or dental handpieces for the performance of treatments involving the application of laser radiation. Such treatments include, inter alia, cutting, or vaporizing, coagulating, sterilizing and promoting healing processes.

A variety of treatments of this type have already been proposed or are in use, and a number of handpieces for delivery of such radiation are already known in the art. Examples of such handpieces are disclosed in "Introduction of New Dental Oral YAG Laser Handpiece and Its Clinical Application", by Yoshida et al, published in May of 1989 in LASERS IN DENTISTRY, Elsevier Science Publishers B.V. (Biomedical Division), and in U.S. Pat. Nos. 4,826,431; 4,849,859; 4,503,853; 4,273,535; and 4,538,609.

It has recently been found that certain treatments, such as the cutting of hard tissue, can be safely performed by applying laser radiation at higher power levels than have been heretofore used. However, the known handpieces are not well suited for conducting radiation at such higher power levels.

SUMMARY OF THE INVENTION

It is a primary object of the present invention to provide handpieces which are suitable for conducting laser radiation at higher power levels.

A more specific object of the invention is to prevent undue heating of the laser optical system within such a handpiece.

Another object of the invention is to facilitate the efficient delivery of radiation from such a handpiece in a moist environment.

Still another object of the invention is to facilitate replacement of an output fiber of such a handpiece.

The above and other objects are achieved, according to the present invention, by a medical or dental handpiece for the performance of laser radiation treatments, comprising: an elongate housing constructed to be held in the hand, the housing having a radiation delivery end and enclosing a chamber which is adjacent the radiation delivery end; radiation conducting means disposed in the housing for conducting laser radiation from a laser source into the chamber and toward the radiation delivery end; and means forming a gas flow path in the chamber for guiding a flow of cooling gas through the chamber in a direction from the radiation conducting means toward the radiation delivery end.

By providing a flow of cooling fluid through the handpiece, and particularly through the chamber which is adjacent the radiation delivery end of the handpiece, those surfaces or bodies which transmit, receive or reflect laser radiation can be effectively cooled, thereby allowing the handpiece to successfully conduct laser radiation having higher power levels. The cooling effect serves, in particular, to prevent damage or deterioration at surfaces from which radiation is reflected or through which radiation passes, and additionally promotes dimensional stability of optical components which act to focus the laser radiation, thereby stabilizing the optical performance of those components.

According to certain embodiments of the invention, the handpiece is equipped for connection to an output fiber into which laser radiation will be directed. In a handpiece according to the invention, the input end of such fiber will automatically be positioned to correctly receive the laser radiation. Such fibers can be made of any suitable material, including consumable, or meltable materials, transparent fibers which are provided with a consumable or meltable coating, etc. Such fibers can have tapered output ends and can be dimensioned to be introduced into a tooth canal, or other small passage where laser radiation treatment is to be performed.

In accordance with other embodiments of the invention, laser radiation is directed from a point within the housing of a handpiece and through a window. Since handpieces of this type frequently operate in humid environments, there will be a tendency for moisture to collect on such a window, with the result that the laser radiation will not be properly focused. In further accordance with the present invention, the gas flow path is arranged to direct the flow of cooling gas along the exterior surface of such a window, to thereby keep that surface free of both soil and moisture.

DESCRIPTION OF THE PREFERRED EMBODIMENTS

Figure 1:
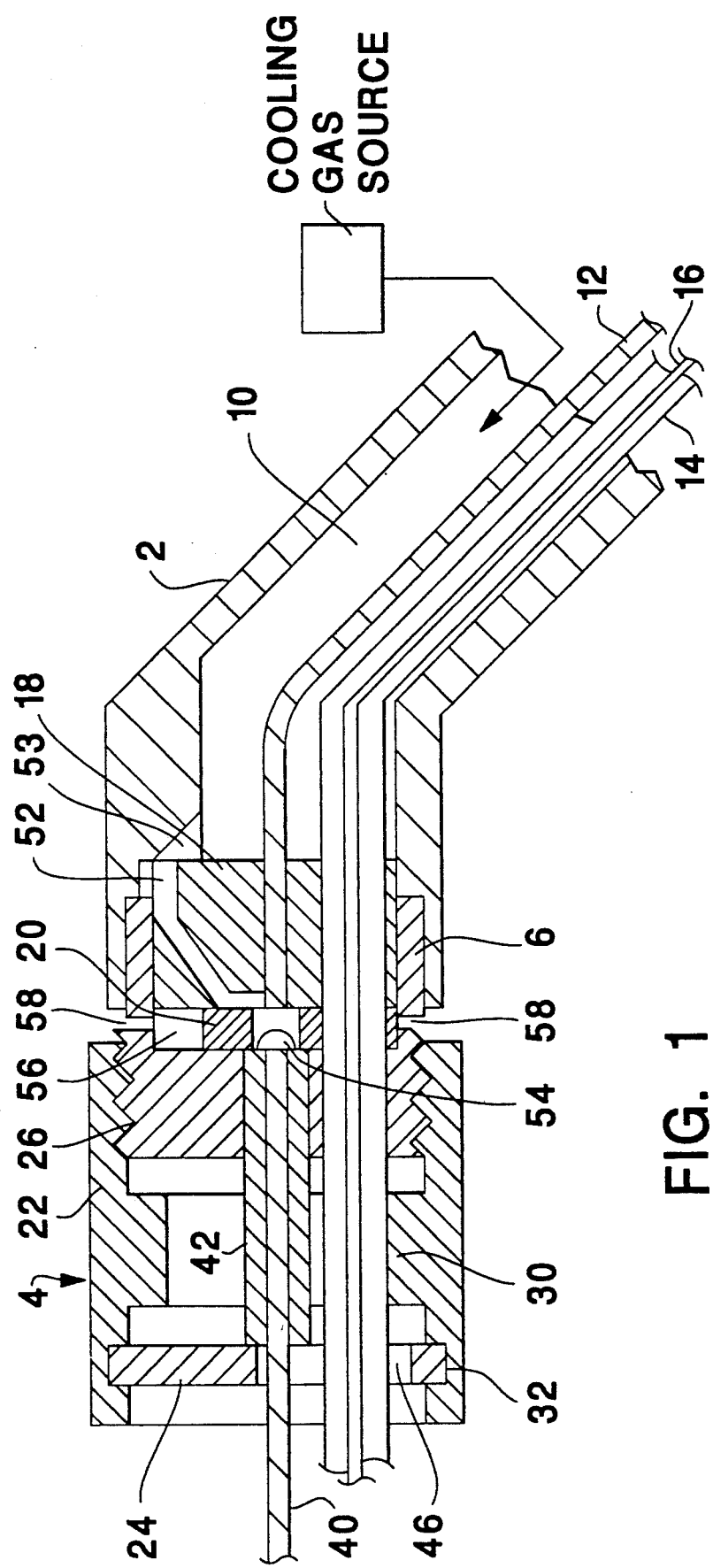
FIGS. 1, 2 and 3 are cross-sectional views of the radiation delivery ends of three embodiments of handpieces according to the present invention.

FIG. 1 shows the tip portion of a handpiece according to a first embodiment of the invention for a disposable, or consumable, optical fiber. The handpiece is composed of a main body, or housing, 2, a cap 4 and a coupling piece 6 via which cap 4 is removably secured to housing 2. Housing 2 encloses a longitudinal channel 10 through which extends an optical fiber 12, an air supply tube 14 and a water supply tube 16 which is enclosed by tube 14.

The distal, or output, end of fiber 12 is secured in a ferrule 18 which is mounted in the distal end of housing 2. The output end face of fiber 12 is polished flush with the corresponding end face of ferrule 18.

A spacer piece 20 is disposed adjacent the last-mentioned end face of ferrule 18 and is provided with an opening surrounding the optical axis of fiber 12 and an opening surrounding tubes 14 and 16.

Coupling piece 6 is installed in a recess in the distal end portion of housing 2, around ferrule 18, with spacer piece 20 interposed between piece 6 and ferrule 18. Coupling piece 6, ferrule 18 and spacer piece 20 may be permanently secured to housing 2.

Cap 4 is constituted essentially by a tube 22 and a front plate 24. The internal wall of tube 22 is provided with a threaded portion for engaging a threaded portion 26 for coupling piece 6. The internal wall of tube 22 is further provided with an annular land, or raised portion, 30 which serves to support tube 14, and with an annular groove 32 for receiving a front plate 24 in a manner to maintain front plate 24 in a desired longitudinal position while allowing that plate to rotate relative to tube 22 about the axis of the tube.

An output optical fiber 40 has one end secured in a second ferrule 42. The other end of fiber 40 is intended to be positioned to administer laser radiation to a region to be treated, e.g. a tooth or gum surface, a tooth canal, etc. Fiber 40 has an input end which is ground flush with the corresponding surface of ferrule 42, which is the surface that will face the output end of fiber 12.

To install a fiber 40 in the handpiece, cap 4 is removed from coupling piece 6 and ferrule 42, with the one end of fiber 40 secured therein, is inserted into a receiving opening provided in coupling piece 6. Cap 4 is then installed by feeding fiber 40 and tubes 14 and 16 through an opening 46 in plate 24 and then screwing tube 22 onto coupling piece 6 while plate 24 remains stationary relative to tubes 14 and 16 until ferrule 42 is pressed firmly between plate 24 and spacer piece 20. When ferrule 42 contacts one face of piece 20 and ferrule 18 contacts the other face of piece 20, the distance between the output end of fiber 12 and the input end of fiber 40 is determined by the thickness of spacer piece 20. Thus, this distance is selected by giving spacer piece 20 a thickness equal to the desired spacing which in practical embodiments is between $25\mu$ and $300\mu$.

In further accordance with the invention, means are provided for directing a dry cooling fluid through the space which separates fibers 12 and 40. In the illustrated embodiment the handpiece is connected to place the hollow interior 10 of housing 2 in communication with a source of dry air under pressure, i.e. a cooling gas source, an air supply channel 52 is formed in ferrule 18 an air passage 53 is formed in the interior wall of housing 2 and an air exit channel is formed by two diametrically opposed passages 54 in spacer piece 20, an annular space 56 around piece 20 and two diametrically opposed outlet passages 58 in coupling piece 6.

Air flowing into the opening in spacer piece 20 between fibers 12 and 40 cools the exposed ends of those fibers and thus helps to prevent damage particularly to the output end of fiber 12. In addition, if during replacement of fiber 40, any moisture should be deposited on the output end of fiber 12, it would be quickly dissipated by the air stream.

Figure 2:
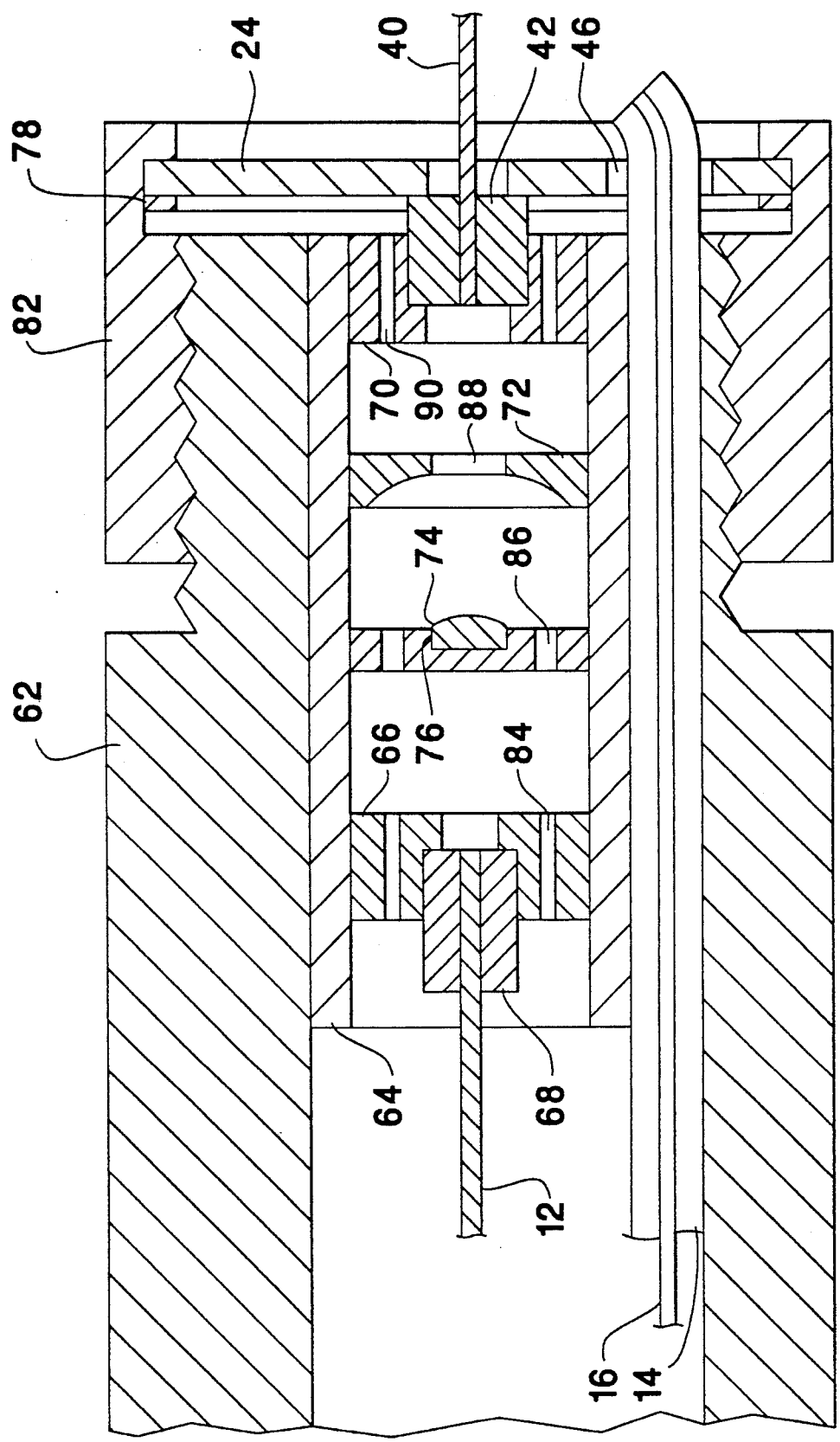

A second embodiment of a handpiece tip for a disposable or consumable optical fiber is shown in FIG. 2. In this embodiment, radiation exiting from fiber 12 is concentrated by two reflecting surfaces onto the input end of disposable fiber 40.

The handpiece includes a main housing 62 which carries a tubular handpiece alignment body 64 and air and water tubes 14 and 16. Alignment body 64 supports a coupling piece 66 for holding a ferrule 68 in which the distal end of fiber 12 is secured. Alignment body 64 additionally supports a coupling piece 70 for holding ferrule 42 of disposable output fiber 40, and an optical system composed of a concave reflecting surface 71 carried by a support body 72 and a convex reflecting surface 73 of an optical element 74 carried by a support body 76 which is transparent to the laser radiation.

The optical system is positioned in alignment body 64 so that when ferrules 42 and 68 are properly seated in their associated coupling pieces 70 and 66, the output end surface of fiber 12 is imaged on the input end surface of fiber 40. As a result, radiation emanating from the output surface of fiber 12 will be concentrated, or focused, on the input surface of fiber 40. Correct positioning of the optical system relative to coupling pieces 66 and 70 is facilitated by the mounting of all of those components in a single alignment body.

As in the case of the embodiment shown in FIG. 1, the handpiece includes a cap composed of a tube 82 and front plate 24 for holding ferrule 42 in a defined position in coupling piece 70. In this embodiment, front plate 24 is held in place by a retaining ring 78.

In order to prevent overheating of handpiece parts along the radiation path, a flow of dry cooling gas, preferably air, is established and maintained through the interior of the handpiece. The air is supplied from a source, which may be the same source that supplied air to tube 14, through the hollow interior of main housing 62 and alignment body 64. The air then flows through longitudinal passages 84 in coupling piece 66, longitudinal passages 86 in support body 76, the axial radiation passage 88 provided in support body 72, longitudinal passages 90 in coupling piece 70 and opening 46 in front plate 24. This air flow will be particularly effective to cool optical element 74 and support body 76. Thermal expansion of these bodies could adversely effect the focusing of radiation on the input end of fiber 40.

As in the case of the embodiment shown in FIG. 1, cap 82 is tightened until ferrule 42 is firmly seated between a seating surface provided in coupling piece 70 and front plate 24, so that the longitudinal, or axial, position of the input end of fiber 40 is accurately positioned. In addition, front plate 24 is rotatable relative to cap 82, so that cap 82 can be threaded onto main housing 62 while front plate 24 is prevented from rotating by its engagement with tube 14.

Figure 3:
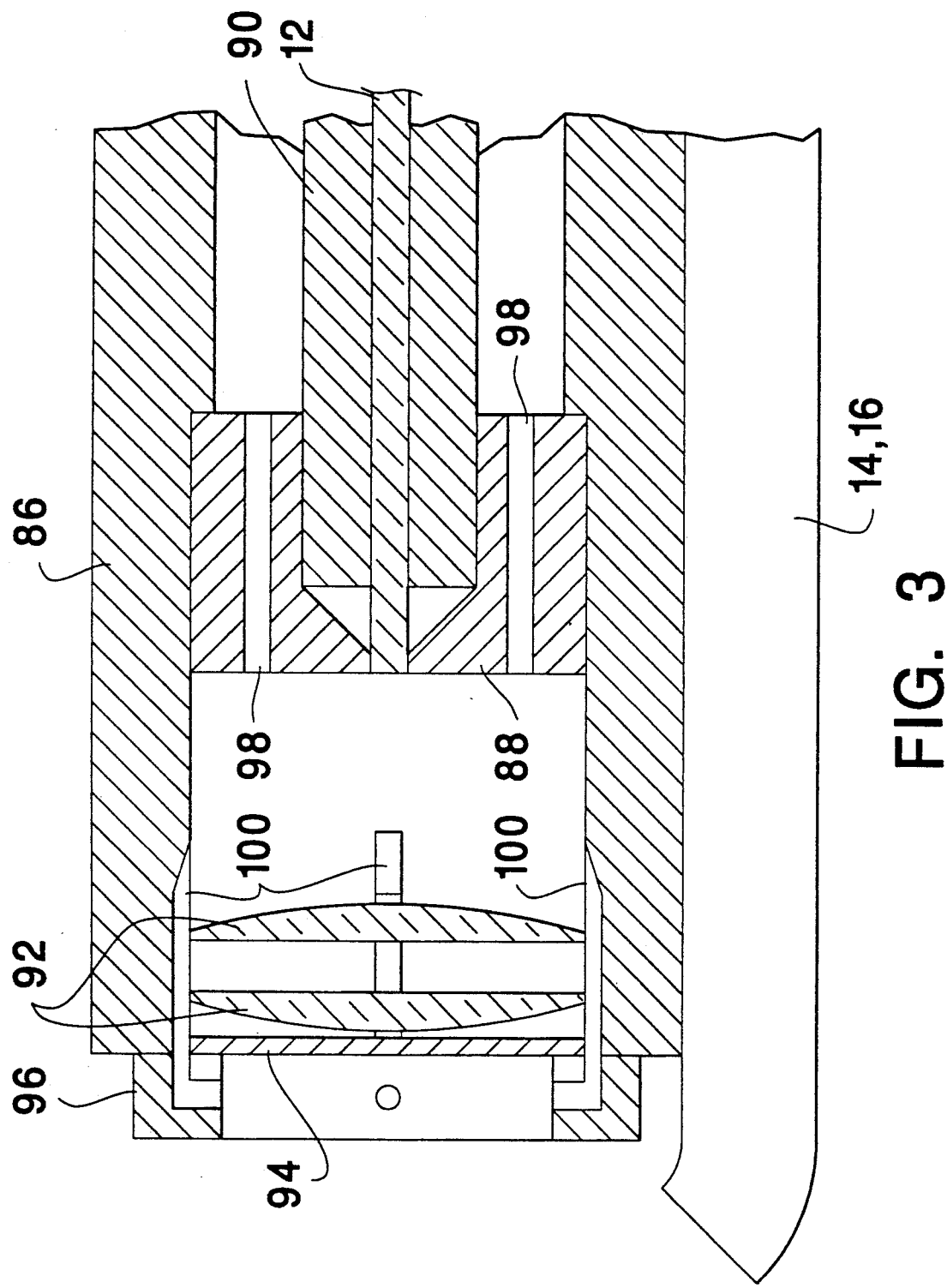

A third embodiment of the present invention is shown in FIG. 3. This embodiment is a non-contact handpiece constructed to focus laser radiation to a spot beyond the distal end of the handpiece. This embodiment includes a housing 86 provided, at the distal end, which is illustrated, with a coupling piece 88 supporting optical fiber 12 which, in this embodiment, is encased in a continuous sheath 90. Such a sheath could also be provided in the embodiments of FIGS. 1 and 2.

The output end of fiber 12 faces an optical system composed of converging lenses 92 which are positioned to focus radiation emanating from the output end of fiber 12 to a location to the left of the distal end of the handpiece. In front of lenses 92, there is disposed a transparent window 94 and an attachment ring 96 which helps to retain window 94 in place. As in the embodiments of FIGS. 1 and 2, housing 86 carries tubes 14 and 16 via which a spray composed of a mixture of air and water may be directed against the region being treated, i.e. the region at which the laser radiation is focused.

During operation of such a handpiece, particularly when the laser radiation has high power levels, the output end of fiber 12 as well as lenses 92, may be subjected to a substantial degree of heating which could damage fiber 12 and/or adversely affect the optical characteristics of lenses 92. In addition, since the distal end of the handpiece will be exposed to a humid environment, it is likely that moisture will accumulate on the exposed surface of window 94, and this can reduce the transmission of radiation through the window as well as having a defocusing effect on the laser radiation.

According to the present invention, these problems are alleviated by the provision of means forming a cooling gas flow path through the interior of the handpiece and past the exposed face of window 94. This gas flow passage is constituted by one or more longitudinal passages 98 in coupling piece 88 and a plurality, for example four, gas flow channels 100 formed in housing 86 and continuing into attachment ring 96. In ring 96, these channels are provided with outlet ends which direct the flow of cooling gas radially inwardly along the exposed surface of window 94.

With the exception of channels 100, the chamber containing lenses 92 and the outlet end of fiber 12 is sealed with respect to the surrounding environment so that as long as gas continues to flow through passages 98 and channels 100, moisture cannot enter that chamber from the region surrounding the handpiece.

In all of the illustrated embodiments of the invention, there can be any desired number of passages for the flow of cooling gas in each of the parts containing such passages and the rate of flow of cooling gas will be selected in accordance with the cooling effect which must be achieved. The cooling gas itself may be air or any other suitable gas having a sufficient heat absorption capability. The handpiece can be constructed so that a flow of cooling gas is maintained as long as laser radiation is being generated and automatic controls can be provided to adjust the rate of flow of cooling gas to the power level at which radiation is being supplied.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

We claim:

1. A medical or dental handpiece for the performance of laser radiation treatments, comprising:
    an elongate housing constructed to be held in the hand, said housing having a radiation delivery end and enclosing a chamber;
    a first optical fiber permanently installed in said handpiece for conducting laser radiation from a laser source into said chamber, said first optical fiber having an output end;
    a disposable optical fiber for guiding laser radiation from said first optical fiber to a region to be treated, said disposable optical fiber having an input end within said chamber;
    fastening means for detachably securing said disposable optical fiber to said housing so that said input end of said disposable optical fiber faces said output end of said first optical fiber when said disposable fiber is secured to said housing;
    a spacer piece interposed between said output end of said first optical fiber and said input end of said disposable optical fiber for establishing a defined distance between said ends, and wherein said spacer piece has an opening through which radiation passes from said output end of said first optical fiber to said input end of said disposable optical fiber; and
    means forming a gas flow path which traverses said opening in said spacer for guiding a flow of cooling gas across said output end of said first optical fiber and said input end of said disposable optical fiber.

2. A handpiece as defined in claim 1 further comprising means carried by said housing for directing a stream of cooling fluid to a body region receiving laser radiation treatment, and wherein said fastening means include a member which secures said fiber to said housing and surrounds said means for directing a stream of cooling fluid.

3. A handpiece as defined in claim 2 wherein said member is mounted to maintain a defined position relative to said means for directing a stream of cooling fluid.

4. A medical or dental handpiece for the performance of laser radiation treatments, comprising:
    an elongate housing constructed to be held in the hand, said housing having a radiation delivery end and enclosing a chamber;
    radiation conducting means disposed in said housing for conducting laser radiation from a laser source into said chamber and toward said radiation delivery end; and
    means forming a gas flow path in said chamber for guiding a flow of cooling gas through said chamber in a direction from said radiation conducting means toward said radiation delivery end;
    wherein: said housing comprises a window which is transparent to radiation produced by the source and through which radiation is directed from said radiation conducting means; said window borders said chamber at said radiation delivery end and has an exterior surface which faces away from said chamber; and said means forming a gas flow path direct the flow of cooling gas out of said chamber and along said exterior surface of said window.

5. A handpiece as defined in claim 4 further comprising optical means disposed in said chamber for directing laser radiation from said radiation conducting means toward said radiation delivery end of said housing.

6. A handpiece as defined in claim 5 wherein said flow path is in thermal communication with said optical means.

7. A handpiece as defined in claim 4 wherein said chamber is adjacent said radiation delivery end of said housing.

* * * * *